United States Patent
Al-Shamma'a et al.

(10) Patent No.: US 10,338,010 B2
(45) Date of Patent: Jul. 2, 2019

(54) METHODS AND APPARATUSES FOR ANALYSING FLUID SAMPLES

(71) Applicant: Liverpool John Moores University, Liverpool (GB)

(72) Inventors: Ahmed Al-Shamma'a, Liverpool (GB); Alex Mason, Liverpool (GB); Olga Korostynska, Liverpool (GB)

(73) Assignee: Liverpool John Moores University, Liverpool (GB)

( * ) Notice: Subject to any disclaimer, the term of this patent is extended or adjusted under 35 U.S.C. 154(b) by 0 days.

(21) Appl. No.: 16/246,666

(22) Filed: Jan. 14, 2019

(65) Prior Publication Data

US 2019/0145908 A1     May 16, 2019

Related U.S. Application Data

(62) Division of application No. 15/667,953, filed on Aug. 3, 2017, now Pat. No. 10,190,995, which is a division of application No. 14/438,022, filed as application No. PCT/GB2013/000450 on Oct. 22, 2013, now Pat. No. 9,766,189.

(30) Foreign Application Priority Data

Oct. 23, 2012  (GB) .................................. 1219029.4

(51) Int. Cl.
*G01N 22/00*     (2006.01)

(52) U.S. Cl.
CPC .................................. *G01N 22/00* (2013.01)

(58) Field of Classification Search
CPC .............................. G01N 22/00; G01N 27/02
See application file for complete search history.

(56) References Cited

U.S. PATENT DOCUMENTS

| | | | | |
|---|---|---|---|---|
| 6,386,053 B1* | 5/2002 | Takeuchi | .................. | B06B 1/06 73/865 |
| 2002/0094531 A1* | 7/2002 | Zenhausern | ........... | C12Q 1/686 435/6.11 |
| 2004/0246079 A1* | 12/2004 | Ehata | ..................... | G01N 22/00 333/219.2 |
| 2014/0001058 A1* | 1/2014 | Ghaffari | ............... | G01N 27/327 205/792 |

FOREIGN PATENT DOCUMENTS

WO     WO 2002/46357      6/2002

* cited by examiner

*Primary Examiner* — Francis C Gray
(74) *Attorney, Agent, or Firm* — Hartman Global IP Law; Gary M. Hartman; Domenica N. S. Hartman

(57) ABSTRACT

A method and apparatus for analyzing a fluid sample that includes loading the sample in a sample space in a sensor with an input and an output, applying an electromagnetic input signal to the input, measuring at the output a response signal that includes an output signal produced by the sensor while the sensor is contacted by the sample and the electromagnetic input signal is applied to the input, comparing the response signal against the electromagnetic input signal to generate a comparison, and matching the comparison against a set of comparisons for known substances.

15 Claims, 3 Drawing Sheets

METHODS AND APPARATUSES FOR ANALYSING FLUID SAMPLES

CROSS REFERENCE TO RELATED APPLICATIONS

This is a division patent application of co-pending U.S. patent application Ser. No. 15/667,953, filed Aug. 3, 2017, which is a division patent application of co-pending U.S. patent application Ser. No. 14/438,022, filed Apr. 23, 2015, which claims the benefit of International Application No. PCT/GB2013/000450 filed Oct. 22, 2013, having a claim of priority to GB patent application number 1219029.4, filed Oct. 23, 2012. The contents of these prior applications are incorporated herein by reference.

BACKGROUND OF THE INVENTION

This invention relates to sensing using electromagnetic waves, in particular, but not exclusively, microwaves, for rapid analysis of substances produced by or during a reaction or other procedure, for example.

GB2203553 discloses a gas sensor having a layer of semiconducting organic polymer such as a polypyrrole that can be exposed to a gas to be detected. An alternating electric signal of varying frequency is applied to conductors bridged by the polymer and the change in impedance characteristic of the sensor when exposed to the gas detected by an impedance analyser. A sensor unit may comprise a number of such sensors of different polymers reacting to different gases. The frequency range used is 1 MHz to 500 MHz.

Known as an 'electronic nose', the gas sensor can be trained using a neural net to recognize different sets of changes in impedance of an array of sensors in response to different gases. GB2203553 suggests that it may be possible to detect particular gases by investigating changes in the impedance characteristic localised at particular frequencies, but notes that it is difficult to do this on account of noise, opting instead for a comparison system in which differences in the variation of impedance characteristics as compared with a reference gas such as nitrogen are determined over a range of frequencies and in particular, not using frequencies above 500 MHz.

This is clearly complex and time consuming, and it would appear also that the impedance characteristics change with time, on a scale of minutes. The method appears suitable only for gases or vapours, and, more particularly, gases or vapours that react with a semiconducting polymer.

BRIEF DESCRIPTION OF THE INVENTION

The present invention provides a robust method and apparatus for detecting or identifying fluids generally, whether they be gases, vapours, liquids or flowing solids, such as powders and to do so in a more convenient way that is not time-dependent.

The invention comprises a method for analysing a fluid sample comprising loading the sample in a sample space in a sensor comprising an input and an output, applying an electromagnetic input signal to the input, measuring at the output a response signal comprising an output signal produced by the sensor while the sensor is contacted by the sample and the electromagnetic input signal is applied to the input, comparing the response signal against the electromagnetic input signal to generate a comparison, and matching the comparison against a set of comparisons for known substances.

The signal may be a microwave signal and may be in the frequency range 1 MHz to 300 GHz and particularly in the range 500 MHz to 300 GHz.

The output signal may be a reflected or transmitted input signal, and the measurement may comprise a measurement of its power and/or phase. The sensor input may be connected as by one or more transmission lines to a microwave generator, and the output to an analyser such as a vector network analyser or a spectrum analyser.

A useful technique involves sweeping the signal across a range of frequencies and detecting a resonance—a peak in the reflected or transmitted signal output. Some samples may exhibit more than one peak, and can be identified by their spectra, in the same way that elements can be identified by their optical spectra.

The invention also comprises an apparatus for analysing a fluid sample, the apparatus including a sensor that includes a sample space for receiving a fluid sample, an input for applying an electromagnetic input signal to the sample, an output connected to the sample space, the capability for measuring an output signal at the output produced by the sensor while the sensor is contacted by the fluid sample and the electromagnetic input signal is applied to the input, and the capability of comparing the output signal against the electromagnetic input signal.

The signal input may be adapted for connection to a signal generator by one or more transmission lines such as coaxial cables, and the signal output may be similarly adapted for connection to an analyser.

The sensor may comprise:
an electrically insulating substrate:
an active conductor layer on the substrate comprising signal input and output electrodes; and
a sample space adapted to accept a fluid sample adjacent the active conductor layer.

The substrate may be on a base conductor layer.

The sample space may have dimensions of the order of size of the electromagnetic wavelength. A 300 GHz microwave has a wavelength of 1 mm, and a sample space of, say, 5 mm square and one or two millimeters deep will give a good response to microwave interrogation.

The active conductor layer may have intercalated or interdigitated input and output electrodes, which may have square, circular, spiral or stellate configuration.

The sample area may be defined by a well holding a known amount of the fluid sample.

In addition, the conductor layer may be covered with a transducer coating,

The transducer coating may be selected or adapted to respond in known manner to electromagnetic waves when in contact with a sample so that the sensor transmits and/or reflects electromagnetic waves in a manner characteristic of the sample.

The frequency range may extend from 9 kHz to 300 GHz, and may comprise the microwave range 300 MHz to 300 GHz or any part or parts of it.

The base conductor layer may be of the same material as the conductor layer on the substrate, or of a different material, either comprising any well-conducting metal such as gold, silver, copper, platinum/gold alloy or a conductive carbon-based material. The electrically insulating substrate may comprise any printed circuit board material, a glass-reinforced epoxy material such as FR4, a glass reinforced PTFE, Duroid® high frequency circuit materials, glass, or alumina, and may be rigid or flexible. The material may have dielectric properties that influence electromagnetic signal decay.

The transducer coating may be selected from metal oxides, polymers, mixtures of oxide and polymer, polymers filled with nanoparticles for enhanced conductivity, and which may operate in the percolation region or near to the percolation threshold. Phosphate and nitrogen binding polymeric hydrogels, as well as cadmium phthalocyanines, may be used. Biological coatings such as enzymes, proteins or even living organisms such as *E. coli* 600 or *Pseudomonas aeruginosa* can also be used. The selected transducer coating may be a stable, general-purpose coating that may survive multiple measurements or may, as particularly with living organisms, be of limited utility, adapted for one or a small number of sample materials and/or reacting with or becoming contaminated by a sample.

Different fluid analytes in contact with the transducer coating will exhibit different responses to microwaves, for example different levels of attenuation, different resonant frequencies, different reflection and transmission characteristics and so forth. Analytes will exhibit different responses when in contact with different transducer coatings.

The invention also comprises a method for analysing a sample by electromagnetic waves in the frequency region extending from 9 kHz to 300 GHz, comprising placing the sample in contact with a transducer coating and measuring a response to electromagnetic waves applied to the transducer coating in the said frequency region. The response may be a resonance at a particular frequency or attenuation of transmitted or reflected radiation.

The response may be measured from a signal reflected back along a transmission line supplying an interrogating signal or from radiated energy picked up by an aerial.

A library of responses may be built up from a series of measurements on different substances, using different transducer coatings, so that substances giving particular responses may be identified. Interrogation may be carried out at particular frequencies in the frequency range, or by a sweep across the range or a part or parts of it.

The applied electromagnetic signal may be controlled by the response, for example, in a feedback loop, to adjust the frequency, for example, to achieve resonance.

The method may be carried out as an element of process control or in a continuous monitoring role, in which samples are introduced robotically.

Methods and apparatus for analysing samples in accordance with the invention will now be described with reference to the accompanying drawings, in which:

DETAILED DESCRIPTION OF THE INVENTION

Figure 1:
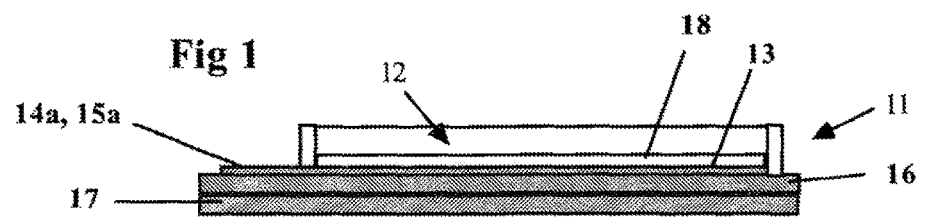
FIG. 1 is a section through one embodiment of sensor.

The drawings illustrate apparatus for analysing a fluid sample providing a sample space 12 in a sensor 11 with input and output electrodes 14, 15 for an electromagnetic signal, and means for measuring an output signal and comparing it against an input signal, and matching the comparison against a set of comparisons for known substances.

The sensor 11 comprises:
an electrically insulating substrate 16:
an active conductor layer 13 on the substrate comprising the signal input and output electrodes 14, 15; and
a well defining the sample space 12 adapted to accept a fluid sample adjacent the active conductor layer 13.

The substrate 16 is on a base conductor layer 17.

Figure 3:
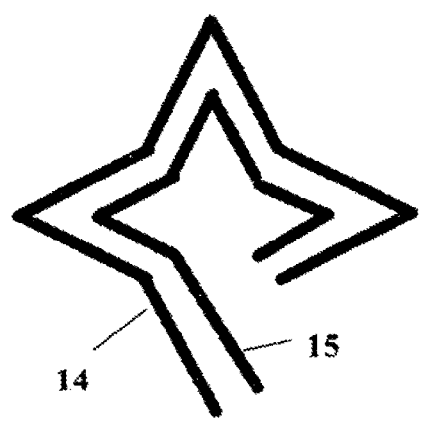
FIG. 3 is a view of one embodiment of a different electrode configuration for the sensor of FIGS. 1 and 2.
Figure 4:
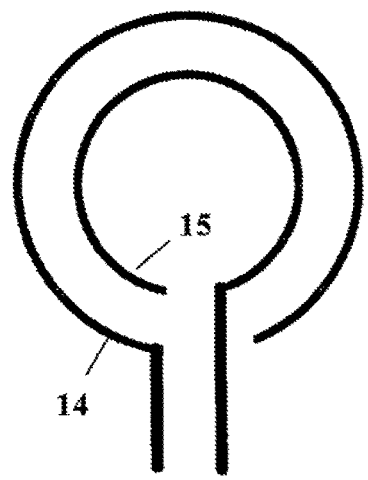
FIG. 4 is a view of another embodiment of electrode configuration for the sensor of FIGS. 1 and 2.

The active conductor layer 13 is in the form of printed intercalated finger electrodes 14, 15 with contact pads 14a, 15a constituting an external connector arrangement. The active conductor layer 13 may be of gold, copper, silver, platinum/gold alloy, conductive carbon material or indeed any of the usual conductor materials, as may the base layer 17, which may be of the same conductor material as the layer 13, or different. The electrode pattern may comprise simple interdigitated fingers as illustrated or more complex patterns such as stellate, as shown in FIG. 3, or circular, as shown in FIG. 4.

Figure 2:
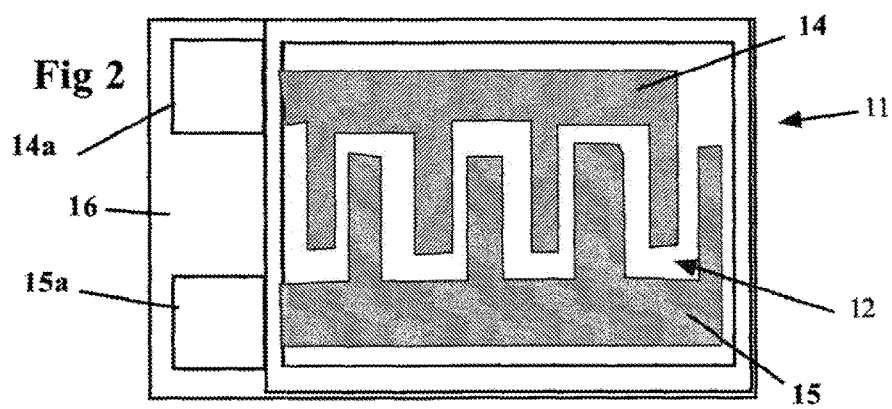
FIG. 2 is a plan view of the sensor of FIG. 1.

The active conductor layer 13 is covered with a transducer coating 18 (not shown in FIG. 2 for illustrative purposes) selected or adapted to respond in known manner to electromagnetic waves in a desired operating frequency range when in contact with a sample so that the sensor 11 transmits and/or reflects electromagnetic waves in a manner characteristic of the sample.

The transducer coating 18 is selected from metal oxides, polymers, mixtures of oxide and polymer, polymers filled with nanoparticles for enhanced conductivity, and which may operate in the percolation region or near to the percolation threshold. Phosphate and nitrogen binding polymeric hydrogels, as well as cadmium phthalocyanines, may be used.

Biological coatings such as enzymes, proteins, even living organisms such as *E. coli* 600 or *Pseudomonas aeruginosa* may be used.

The selected transducer coating 18 may be a stable, general-purpose coating that may survive multiple measurements or may be of limited utility, adapted for one or a small number of sample materials and/or reacting with or becoming contaminated by a sample.

The transducer coating 18 may serve only to insulate the conductor layer from the sample, but may also influence the sensor response to the signal, without necessarily reacting or interacting in any physical or chemical way with the sample.

The operating frequency range may extend from 9 kHz to 300 GHz, and may comprise the microwave range 300 MHz to 300 GHz or any part or parts of it. The size of the sample space is commensurate with the signal wavelength, and 300 GHz signal having a free-space wavelength of 1 mm, the sample space being typically a few millimeters, say five to ten millimeters square and typically one or two millimeters deep, for example, an area between 20 and 50 square millimeters with a volume between 20 and 100 cubic millimeters.

The electrically insulating substrate 16 comprises any printed circuit board material, a glass-reinforced epoxy material such as FR4, a glass reinforced PTFE, Duroid® high frequency circuit materials, glass, or alumina, and may be rigid or flexible. The material may have dielectric properties that influence electromagnetic signal decay.

Figure 5:
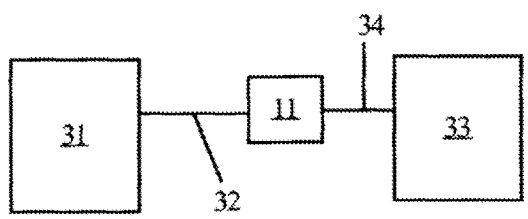
FIG. 5 is a diagrammatic illustration of a sensor connected in a measuring system.

FIG. 5 illustrates a sensor 11 in a measuring system comprising an EM generator 31 connected via a cable 32 or by radiating microwaves or both and an analyser 33 connected by a cable 34 and/or radiating microwaves. The EM generator 31 comprises a tunable microwave generator having a frequency range of 9 kHz to 300 GHz, and the analyser 33 is adapted to measure power and/or phase in this frequency range transmitted through the sensor 11.

Figure 6:
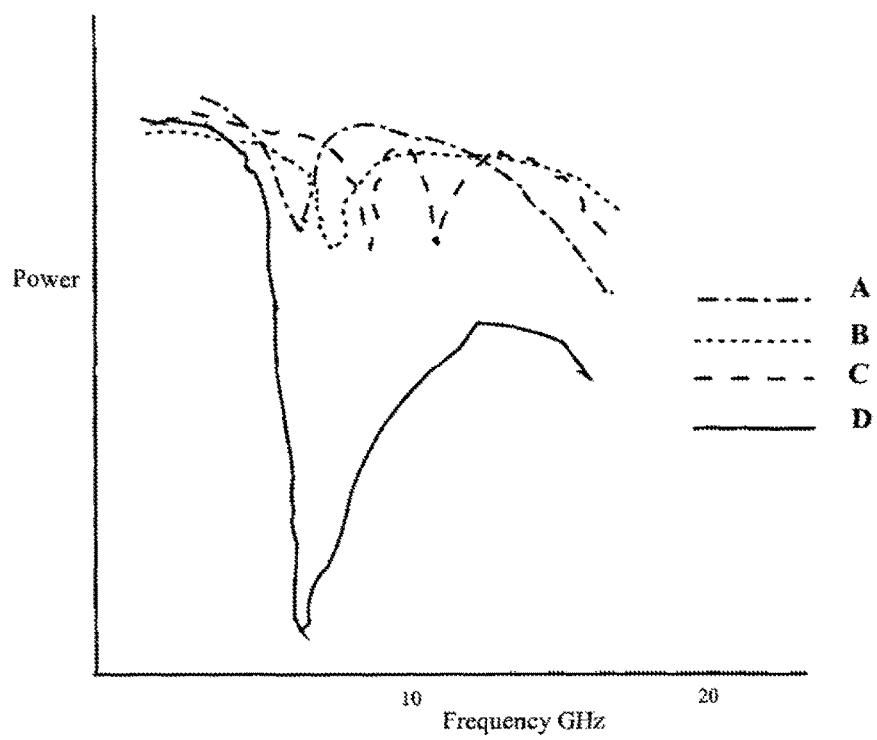
FIG. 6 is a graphical display of power against frequency for particular sensor configurations with a particular analyte.

FIG. 6 is a graphical display showing transmitted power against microwave frequency in a sweep from zero to 15 GHz for a sensor 11 in which the transducer coating 18 is hydroxyapatite and the analyte is isopropyl alcohol (IPA). Trace A is for the sensor without either the transducer coating or the IPA, trace B is for the coating 18 without the IPA, trace C is for the sensor without the coating but with the IPA, and trace D is for the sensor with both transducer coating 18 and IPA. This latter trace D shows a marked resonance at 7.5 GHz.

Different fluid samples in contact with different transducer coatings will exhibit different responses to microwaves, for example different levels of attenuation, different resonant frequencies, different reflection and transmission characteristics and so forth. For any particular application, for detecting a particular analyte or one or more of a number of possible analytes, there will be a suitable choice of the transducer coating 18.

Sensors as described can be fashioned in different sizes and configurations using different materials to adapt them to identifying and measuring properties of different substances. A sensor used to identify and measure one class of substances, say oils, will be designed so as to be particularly responsive to substances of that class and operated within a frequency range that includes resonant frequencies of such substances. A library of responses to a frequency sweep for substances of that class can be built up and referred to for identifying such substances when presented.

The sensors might be used in quality control, moreover, properties of samples from production being measured to test conformity from a standard.

The invention claimed is:

1. A method for analysing a fluid sample, the method comprising:
    loading the sample in a sample space in a sensor comprising an input and an output;
    applying an electromagnetic input signal to the input;
    controlling the electromagnetic input signal in a feedback loop, to adjust the frequency of the electromagnetic input signal;
    measuring at the output a response signal comprising an output signal produced by the sensor while the sensor is contacted by the sample and the electromagnetic input signal is applied to the input;
    comparing the response signal against the electromagnetic input signal to generate a comparison; and
    matching the comparison against a set of comparisons for known substances.

2. A method according to claim 1, further comprising controlling the electromagnetic input signal to achieve resonance.

3. A method according to claim 1, carried out as an element of process control or in a continuous monitoring role, in which samples are introduced robotically.

4. Apparatus for analysing a fluid sample, the apparatus including a sensor comprising:
    a sample space for receiving a fluid sample;
    an input for applying an electromagnetic input signal to the sample;
    an output connected to the sample space;
    an electrically insulating substrate;
    an active conductor layer on the substrate comprising signal input and output electrodes of, respectively, the input and output of the sensor, wherein the sample space is adjacent the active conductor layer;
    a transducer coating covering the conductor layer and adapted to respond in known manner to electromagnetic waves when in contact with known substances so that the sensor transmits and/or reflects electromagnetic waves in a manner characteristic of the known substances;
    measurement means for measuring an output signal at the output produced by the sensor while the sensor is contacted by the fluid sample and the electromagnetic input signal is applied to the input; and
    means for comparing the output signal against the electromagnetic input signal.

5. Apparatus according to claim 4, wherein the sample space has a volume between 20 and 100 cubic millimeters.

6. Apparatus according to claim 4, wherein the sample space has an area between 20 and 50 square millimeters.

7. Apparatus according to claim 4, wherein the substrate is on a base conductor layer.

8. Apparatus according to claim 7, wherein the base conductor layer is of the same material as the active conductor layer.

9. Apparatus according to claim 7, wherein the base conductor layer is of a different material from the active conductor layer, either comprising any well-conducting metal such as gold, silver, copper, platinum/gold alloy or a conductive carbon-based material.

10. Apparatus according to claim 4, wherein the input and output electrodes have intercalated or interdigitated patterning.

11. Apparatus according to claim 4, in which the transducer coating is selected from metal oxides, polymers, mixtures of oxide and polymer, polymers filled with nanoparticles for enhanced conductivity.

12. Apparatus according to claim 4, in which the transducer coating comprises phosphate and nitrogen binding polymeric hydrogels or cadmium phthalocyanines.

13. Apparatus according to claim 4, in which the transducer coating comprises a biological material such as an enzyme or a protein, or a living organism such as *E. coli* 600 or *Pseudomonas aeruginosa*.

14. Apparatus according to claim 4, in which the transducer coating is a stable, general-purpose coating that will survive multiple measurements.

15. Apparatus according to claim 4, in which the transducer coating is of limited utility, adapted for one or a small number of sample materials and/or reacting with or becoming contaminated by a sample.

* * * * *